United States Patent
Lim et al.

(10) Patent No.: US 8,360,078 B2
(45) Date of Patent: Jan. 29, 2013

(54) COMPACT SYSTEM WITH MAGNETIC SLIDE OUT BRUSH

(75) Inventors: Cindy Lim, Santa Monica, CA (US); Megan Rene Langdon, Santa Monica, CA (US)

(73) Assignee: HCT Asia Ltd, Central (HK)

( * ) Notice: Subject to any disclaimer, the term of this patent is extended or adjusted under 35 U.S.C. 154(b) by 187 days.

(21) Appl. No.: 12/823,748

(22) Filed: Jun. 25, 2010

(65) Prior Publication Data

US 2011/0315161 A1  Dec. 29, 2011

(51) Int. Cl.
*A45D 42/02* (2006.01)
(52) U.S. Cl. .................................................... 132/301
(58) Field of Classification Search .......... 132/293, 132/294, 301, 304, 305; 206/581, 823
See application file for complete search history.

(56) References Cited

U.S. PATENT DOCUMENTS

| | | | |
|---|---|---|---|
| 5,107,984 A | 4/1992 | Welschoff | |
| 5,330,056 A * | 7/1994 | de la Rocha | 206/581 |
| 5,482,059 A | 1/1996 | Miraglia | |
| 6,070,597 A | 6/2000 | Motherhead | |
| 6,189,697 B1 | 2/2001 | Davis | |
| 6,283,298 B1 | 9/2001 | Seidler | |
| 6,532,970 B2 | 3/2003 | Phue | |
| 6,546,937 B2 | 4/2003 | Gueret | |
| 6,588,958 B1 | 7/2003 | Seidler | |
| 6,669,389 B2 | 12/2003 | Gueret | |
| 6,831,541 B1 | 12/2004 | Seidler | |
| 6,866,046 B2 | 3/2005 | Gueret | |
| 7,261,483 B2 | 8/2007 | Gueret | |
| 7,344,327 B2 | 3/2008 | Gueret | |
| 7,866,758 B2 | 1/2011 | Jang | |
| 7,918,620 B2 | 4/2011 | Del Ponte | |
| 8,074,666 B2 | 12/2011 | Piao | |
| 8,132,285 B2 | 3/2012 | Piao | |
| 8,185,998 B2 | 5/2012 | Xu | |
| 2007/0261710 A1 * | 11/2007 | Son et al. | 132/293 |
| 2008/0078419 A1 | 4/2008 | Hirst | |
| 2010/0037407 A1 | 2/2010 | Telwar | |
| 2010/0043815 A1 * | 2/2010 | Levy et al. | 132/200 |

FOREIGN PATENT DOCUMENTS

JP  2003033228 A  2/2003
KR  200432010 Y1  11/2006

OTHER PUBLICATIONS

Givenchy Parfums Maquillage, Soins, Parfums, retrieved on May 14, 2010 at <<http://www.parfumsgivenchy.com/make_up/collections/2010_summer_collection/products_in_this_collection/le_prisme_yeux_island_camaieu_limited_edition/product_5_183_1128_214.html>> 1 page.

Givenchy Summer Makeup Collection 2010 Review and Swatches, retrieved on May 14, 2010 at <<http://www.musingsofamuse.com/2010/04/givenchy-summer-makeup-collection-2010-review-and-swatches.html>> 20 pages.

* cited by examiner

*Primary Examiner* — Rachel Steitz
(74) *Attorney, Agent, or Firm* — Lee & Hayes, PLLC

(57) ABSTRACT

A compact system for applying a product to a surface including a removable applicator slideably housed in a compact comprising an actuator and a slide-mechanism. In one example, the slide-mechanism is configured to magnetically couple with a magnet in the base of the applicator, and slides the applicator into and out of the compact. By virtue of having a removable applicator, the compact system is portable and convenient, while at the same time the applicator remains clean and intact until a time of use.

25 Claims, 5 Drawing Sheets

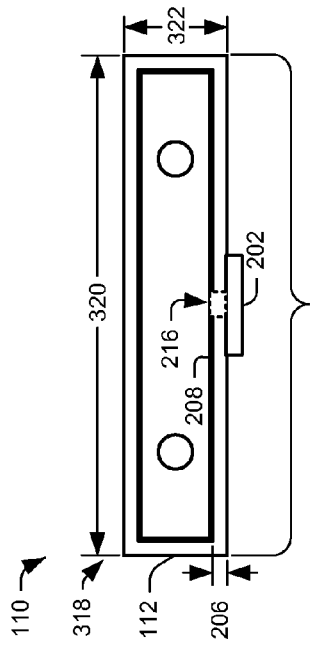
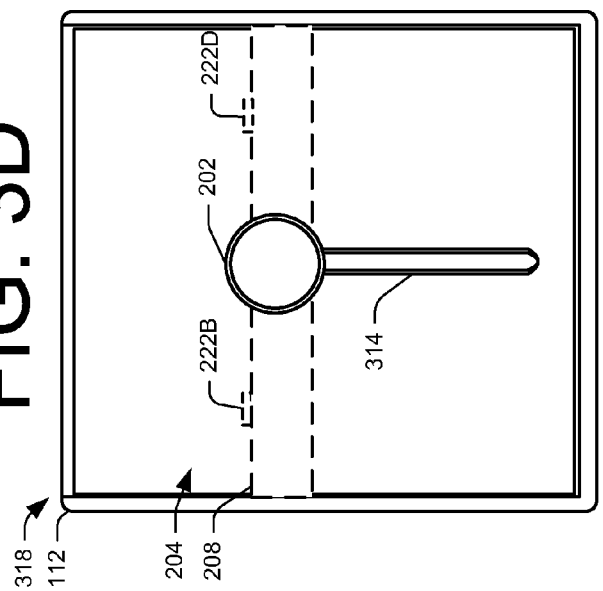
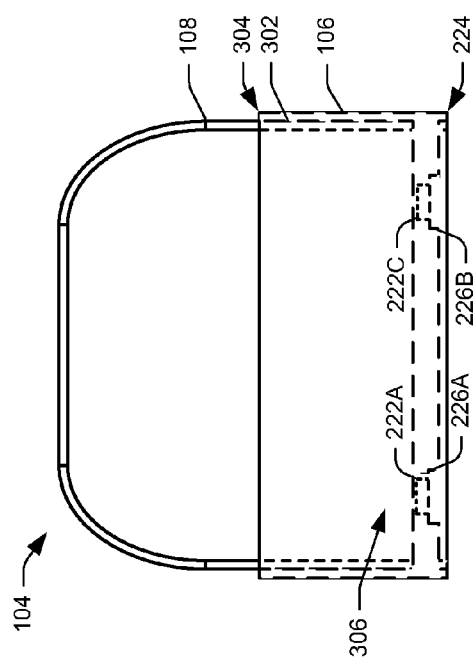
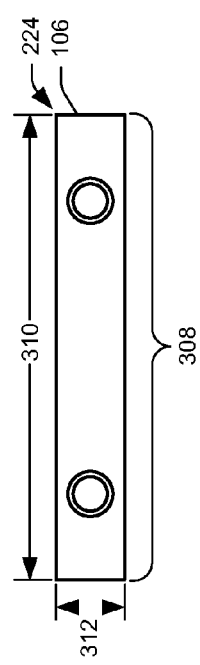

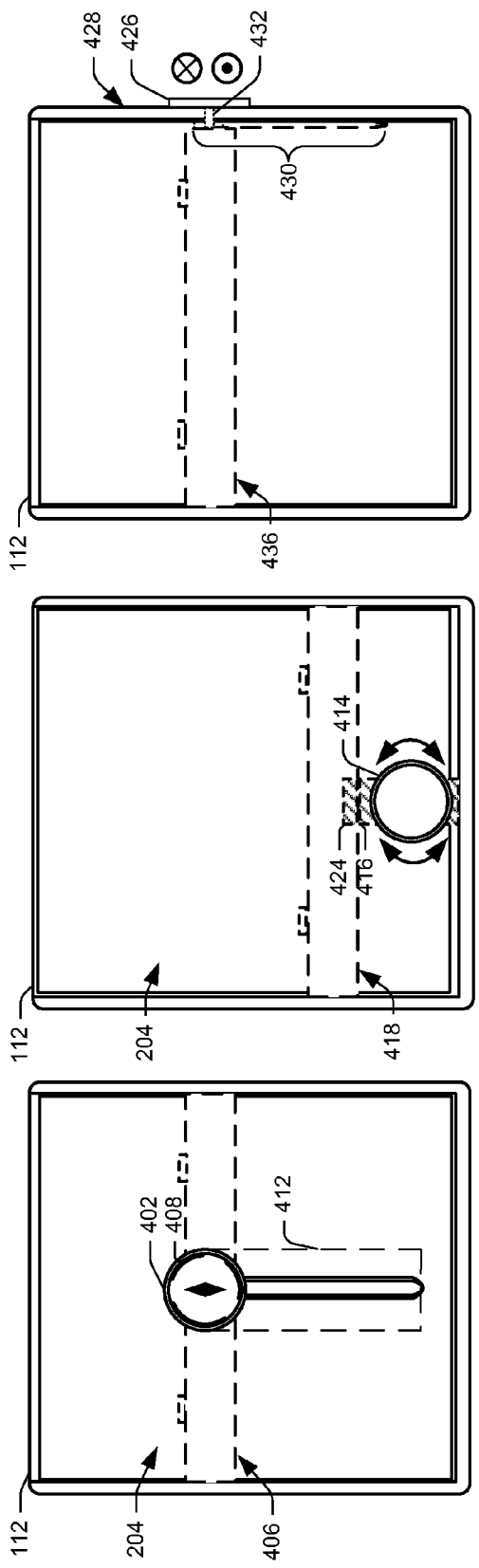

COMPACT SYSTEM WITH MAGNETIC SLIDE OUT BRUSH

BACKGROUND

Compact systems exist for housing cosmetic or medicinal products, along with a brush for applying cosmetics or medicinal products to the body. For example, one compact system may employ a pot in one portion of the compact system, along with a loose brush housed in another portion of the compact system (i.e., a pot housed in a first half of the compact system and a loose brush housed in a second half of the compact system). Further, another compact system may be designed to contain a product and a brush housed in the same portion of the compact system (i.e., a pot and a brush housed in the same portion of the compact system).

However, existing compact systems that contain both a product and a brush consume more space than existing compacts containing an individual product. Also, the brush is not retained and may fall out or become lost from the compact system. Further, existing compact systems are not conducive to preventing contamination of a brush, when the compact system is designed to house the brush along with the product. Accordingly, there remains a need in the art for improved compact systems that provide the portability and convenience of a compact, while preventing contamination and damage of a brush.

BRIEF DESCRIPTION OF THE DRAWINGS

The detailed description is set forth with reference to the accompanying figures. In the figures, the left-most digit(s) of a reference number identifies the figure in which the reference number first appears. The use of the same reference numbers in different figures indicates similar or identical items.

FIG. 3A and FIG. 3B depict a back side view and a bottom view, respectively, of the illustrative magnetic brush shown in FIG. 1, while FIG. 3C and FIG. 3D depict a back side view and a top view, respectively, of the illustrative compact shown in FIG. 1.

FIG. 4A and FIG. 4B, illustrate a back view and a top view of the compact illustrated in FIG. 1, respectively, comprising a magnetic knob actuator and respective slide-mechanism that may be used in the arrangement of components shown in FIG. 2A, FIG. 2B, and FIG. 2C.

FIG. 4C and FIG. 4D, illustrate a back view and a top view of the compact illustrated in FIG. 1, respectively, comprising a dial and magnet actuator, and respective slide-mechanism that may be used in the arrangement of components shown in FIG. 2A, FIG. 2B, and FIG. 2C.

FIG. 4E and FIG. 4F illustrate a back view and a top view of the compact illustrated in FIG. 1, respectively, comprising a dial and gear mechanism actuator, and respective slide-mechanism that may be used in the arrangement of components shown in FIG. 2A, FIG. 2B, and FIG. 2C.

DETAILED DESCRIPTION

Overview

Figure 1:
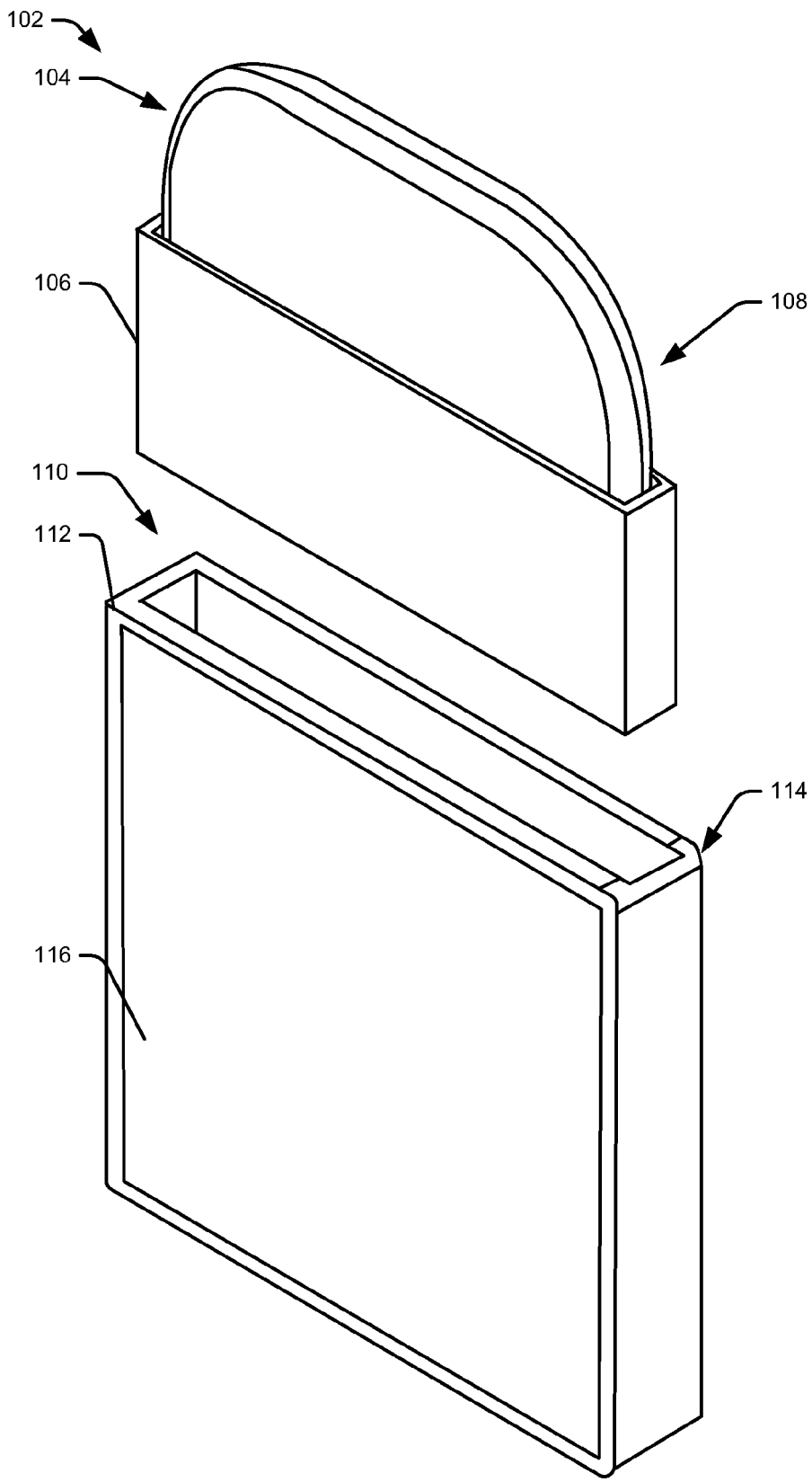
FIG. 1 depicts an isometric view of an illustrative compact system for applying a product to a body.

This application describes compact systems comprising compacts removably housing applicators. By virtue of having applicators removably housed in a compact, devices according to this disclosure are adaptable to conveniently and portably house applicators until a time of use. For example, a user may protectively house a magnetic brush in a compact system and subsequently store the compact system in a personal effect (e.g., a purse) until a time of use. The compact system retains the applicator within the compact while in non-use so that it will not become lost. While stored in the purse, the compact system will keep the brush clean and intact until the user desires to apply or retouch a makeup product to portions of the user's body.

Generally, a compact system according to this disclosure comprises a compact having a slide-mechanism housed within the compact and a removable applicator coupled to the slide-mechanism. The compact generally includes an actuator disposed on an outer surface of a wall of the compact for selectively sliding the slide-mechanism and likewise the applicator into and/or out of the compact.

While the applicator is described in various embodiments herein as a brush, other types of applicators may also be used, such as, for example, a sponge, flocking, a comb, a combination of any of the foregoing, or the like. Also, while the applicator is described throughout the application as being removably retained within the compact by a magnetic retention mechanism, other types of retention mechanisms may also be used, such as, for example, an interference fit, a snap fit, a clip, or any other suitable retention mechanism.

In one example, in which the applicator comprises a brush retained by a magnetic retention mechanism, the slide-mechanism may slide the magnetic brush from a stored position to an accessible position. In the stored position, the magnetic brush is protectively housed within the compact to prevent contamination and/or damage of the magnetic brush. In the accessible position, a portion of the magnetic brush protrudes distally from the compact, where a user may grip the protruding portion and decouple the magnetic brush from the slide-mechanism. In this embodiment, the removable brush includes a flat rectangular base having a group of bristles fixed to a top of the base and a magnet disposed in a bottom of the base. Further, the slide-mechanism may have a magnet fixed to a portion of the slide-mechanism for magnetically coupling to the magnetic brush. The compact system may also include a mirror disposed on an outside surface of the compact and/or a compartment arranged between the mirror and the other wall for containing a product behind the mirror.

In various embodiments, the slide-mechanism described herein may be actuated by any suitable actuation mechanism, such as, for example, a gripable portion (e.g., a rectangular bar, a disk-shaped knob or nodule, or the like) slideably disposed on an exterior surface of the compact, a magnetic knob slideably disposed on the exterior surface of the compact, a dial disposed on the exterior surface of the compact, a push-button disposed on an exterior surface of the compact, or the like. In embodiments that employ a brush applicator, various embodiments of the brush are also contemplated. For example, the brush may comprise a group of hairs that are natural (e.g., animal), synthetic (e.g., plastic or rubber), or the like. Further, the brush may comprise a single unit of bristles over-molded to a base of the brush and be formed of plastic. For example, the brush may comprise a single unit of shaft-shaped bristles over-molded to the base of the brush, a single unit of blade-shaped bristles over-molded to the base of the brush, or the like.

Illustrative Compact System with Removable Magnetic Brush

FIG. 1 depicts an illustrative compact system 102. The compact system 102 includes a removable brush 104 with a flat rectangular base 106, which may be formed of metal, plastic (e.g., polypropylene (PP), acrylonitrile butadiene styrene (ABS), Polyoxymethylene (POM)), glass, wood, and/or any other suitable material, for fixing a group of bristles 108 thereto. While in the illustrated embodiment, the removable brush 104 is illustrated as comprising a flat fan-shaped group of bristles 108 for application of a product such as blush, the group of bristles 108 according to this disclosure may also be used to apply other products, such as foundation, mascara, or other cosmetic products and may take on other shapes, such as having multiple flat fan-shaped group of bristles, a flat rectangular-shaped group of bristles, multiple flat rectangular-shaped groups of bristles, a few individual larger bristles, or the like. Moreover, as discussed above, other, non-brush type applicators may also be used (e.g., sponges, flocking, comb, etc.).

As illustrated, compact assembly 102 may comprise a substantially flat rectangular-shaped compact 110, which may be formed of metal, plastic (e.g., polypropylene (PP), acrylonitrile butadiene styrene (ABS), Polyoxymethylene (POM)), glass, wood, and/or any other suitable material, for slideably housing a magnetic brush. FIG. 1 further illustrates a shell 112 defining a cavity 114 for removeably housing the magnetic brush 104. Magnetic brush 104 is illustrated as having a shape complimentary to that of the cavity 114, such that the cavity 114 is suitable for receiving and guiding the magnetic brush 104 into or out of the compact 110. Cavity 114 may be rectangular-shaped or any other suitable shape to provide for linearly sliding the magnetic brush 104 into or out of the compact 110. Here, FIG. 1 illustrates a mirror 116 disposed on an exterior surface of the shell 112.

Figure 2A:
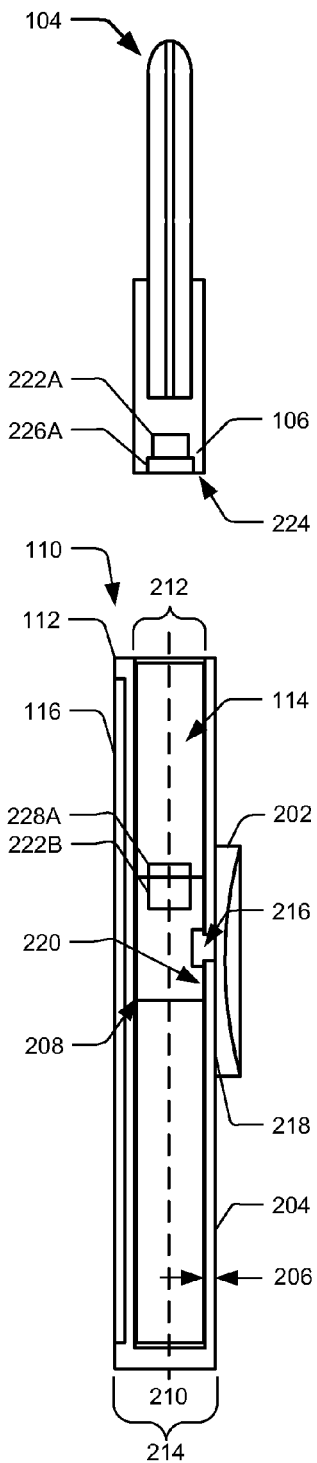
FIG. 2A, FIG. 2B, and FIG. 2C depict right side views of the illustrative compact system shown in FIG. 1, with the removable magnetic brush in a decoupled position, an accessible position, and a stored position, respectively.
Figure 2B:
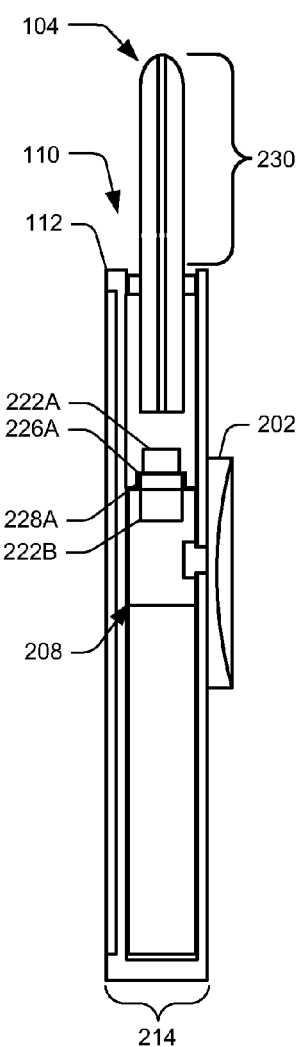
Figure 2C:
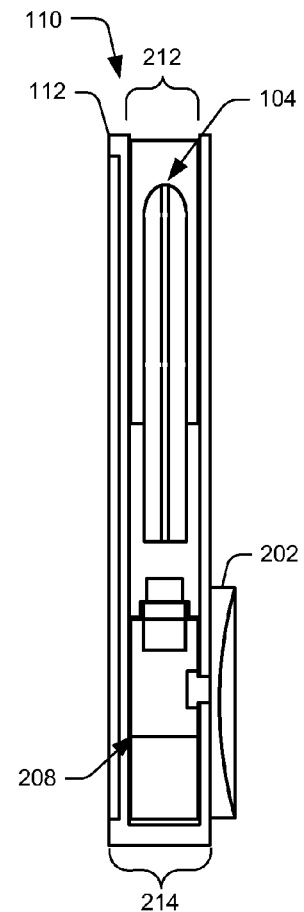

FIG. 2A, FIG. 2B, and FIG. 2C depict right side views of the illustrative compact system shown in FIG. 1 with the removable magnetic brush 104 in a decoupled position, an accessible position, and a stored position, respectively. FIG. 2A depicts a right side view of the illustrated compact system 102 shown in FIG. 1 with the magnetic brush 104 decoupled from the compact 110. The compact 110 is illustrated as comprising an actuator 202 that, in this example, is configured, as a knob-shaped actuator 202. The actuator 202 is illustrated as being disposed on an exterior surface 204 of a wall 206 of the shell 112 for selectively displacing a slide-mechanism 208 slideably housed in the shell 112 linearly in a longitudinal direction 210. When the actuator 202 is displaced along longitudinal direction 210, the slide-mechanism 208 is either displaced proximate to an opening 212 of the cavity 114 arranged in the shell 112 or displaced proximate to a closed bottom end 214 of the shell 112. Here, FIG. 2A illustrates the actuator 202 being displaced proximate to the opening 212. FIG. 2A further illustrates the brush 104 being decoupled from the slide-mechanism 208. While FIG. 2A illustrates a knob-shaped actuator 202, alternative shaped actuators are conceptualized. For example, actuator 202 may be bar-shaped, disc-shaped, rectangular-shaped, or the like. FIG. 2A further illustrates a linkage 216 configured to be received by an opening disposed in wall 206 and fixed to a bottom 218 of the actuator 202 and to a top 220 of the slide-mechanism 208. Further, while FIG. 2A illustrates a slide-mechanism 208 coupled to an actuator 202 by a linkage 216, any suitable coupling mechanism, such as, for example, by a magnetic coupling mechanism, a gear coupling mechanism, a spring coupling mechanism, or the like, suitable for displacing the slide-mechanism 208 are contemplated.

In the illustrated example, brush 104 is illustrated as comprising a magnet 222A fixed to a bottom 224 of the base 106 of the brush 104 for magnetically coupling to another magnet 222B fixed to a portion of the slide-mechanism 208. Further, as illustrated in FIG. 2A, brush 104 may comprise an opening 226A for receiving a protruding portion 228A of the other magnet 222B.

FIG. 2B depicts the right side view of the illustrated compact system 102 shown in FIG. 1 with the brush 104 in an accessible position. With the brush 104 in an accessible position, a portion 230 of the brush 104 is exposed providing a user an area to grip the exposed portion 230 of the brush 104 at a time of use. Further, FIG. 2B illustrates magnet 222A magnetically coupled to magnet 222B, as well as illustrates the opening 226A receiving the protruding portion 228A of the other magnet 222B. With magnet 222A magnetically coupled to the other magnet 222B, the brush 104 is defined to be removeably coupled to compact 110.

FIG. 2C depicts the right side view of the illustrated compact system 102 shown in FIG. 1 with the brush 104 in a stored position. When the brush 104 is in a stored position, the brush 104 is protectively housed inside the shell 112 of the compact 110 to prevent contamination and/or damage of the brush 104. Again, and as discussed above, magnet 222A is magnetically coupled to the other magnet 222B, which keeps the brush 104 coupled to the slide mechanism 208, and housed in the compact 110 until a time of use. Further, and as illustrated in FIG. 2C, actuator 202 is linearly displaced in the longitudinal direction 210 proximate to the bottom end 214 of the compact 110.

FIG. 3A illustrates a back side view of the illustrative magnetic brush 104 of the compact system 102 shown in FIG. 1. FIG. 3B illustrates a bottom view of the base 106 of the brush 104 illustrated in FIG. 3A. FIG. 3C illustrates a back side view of the illustrative compact 110 shown in FIG. 1. FIG. 3D illustrates a top view of the compact 110 illustrated in FIG. 3C.

The back side view shown in FIG. 3A illustrates a group of bristles 108 being fixed in a pocket 302 in a top 304 of the base 106 of the brush 104. FIG. 3A also illustrates a gripping portion 306 of the bottom 224 of the base 106 opposite to the group of bristles 108 in the top 304 of the base 106. Further, FIG. 3A illustrates magnets 222A and 222B fixed to the gripping portion 306 of the bottom 224 of the base 106. While FIG. 3A illustrates two substantially circular magnets 222A and 222B fixed to the gripping portion 306 of the bottom 224 of the base 106, any quantity of magnets or shape of magnets, or the like, are contemplated. For example, a single flat rectangular-shaped magnet, two oval-shaped magnets, three triangular-shaped magnets, or the like, may be fixed to the gripping portion 306 of the bottom 224 of the base 106. Further, while FIG. 3A illustrates magnets 222A and 222C being arranged in openings 226A and 226B, respectively, magnets 222A and 222C may not be arranged in openings. For example, magnets 222A and 222C may be arranged on the gripping portion 306 such that they are substantially flush with a bottom surface, where the bottom surface is void of any pockets, indents, or the like.

FIG. 3B illustrates a bottom view of the base 106 of brush 104. The bottom view shown in FIG. 3B illustrates a substantially flat body of the base 106, and likewise a substantially flat rectangular-shape of the brush 104. Further, the bottom view shown in FIG. 3B illustrates a substantially rectangular cross-section 308 as viewed from the bottom 224. More specifically, FIG. 3B illustrates the rectangular cross-section 308 of the base 106 as viewed from the bottom 224 comprising a width 310 of approximately 52 millimeters and a height 312 of approximately 5 millimeters. While FIG. 3B illustrates the rectangular cross-section 308 as comprising a width 310 of approximately 52 millimeters and a height 312 of approximately 5 millimeters, any width and height combinations are appropriate for producing a thin or slender rectangular cross-section 308 are contemplated. For example, any cross-section 308 as viewed from the bottom 224 comprising a width of approximately ten times longer than a height, or the like, are acceptable.

The back side view of the illustrative compact 110 shown in FIG. 3C illustrates the actuator 202 being disposed on the exterior surface 204 of the wall 206 of the shell 112 for selectively displacing a slide-mechanism 208 slideably housed in the shell 112. FIG. 3C further illustrates a slot 314 disposed in the exterior surface 204 of the shell 112. As described above, the linkage 216 is configured to be received by the slot 314 disposed in the wall 206 and fixed to the bottom 218 of the actuator 202 and to the top 220 of the slide-mechanism 208. Similarly, and as discussed above, while FIG. 3C illustrates two substantially circular magnets 222B and 222D fixed to the slide-mechanism 208, any quantity of magnets or shape of magnets, or the like, are contemplated. For example, a single flat rectangular-shaped magnet, two oval-shaped magnets, three triangular-shaped magnets, or the like, may be fixed to the slide-mechanism 208. Further, while FIG. 3C illustrates magnets 222B and 222D protruding from the slide-mechanism 208, magnets 222B and 222D may be arranged in the slide-mechanism 208 such that they are substantially flush with the surface of the slide-mechanism 208.

FIG. 3D illustrates a top view of the compact 110. The top view shown in FIG. 3D illustrates a substantially flat body of the shell 112, and likewise a substantially flat rectangular-shape of the compact 110. Further, the top view shown in FIG. 3D illustrates a substantially rectangular cross-section 316 as viewed from a top 318 of the compact 110. More specifically, FIG. 3D illustrates the rectangular cross-section 316 of the compact 110 as viewed from the top 318 comprising a width 320 of approximately 55 millimeters and a height 322 of approximately 8 millimeters. While FIG. 3D illustrates the rectangular cross-section 316 as comprising a width 320 of approximately 55 millimeters and a height 322 of approximately 8 millimeters, any width and height are appropriate that produce a thin or slender rectangular cross-section 316. For example, where the cross-section 316 as viewed from the top 318 comprises a width approximately seven times that of a height, or the like, are acceptable.

FIG. 4A and FIG. 4B, FIGS. 4C and 4D, and FIG. 4E and FIG. 4F illustrate back views and top views, respectively, of other actuators that may be used in the arrangement of components shown in FIG. 2A, FIG. 2B, and FIG. 2C to linearly displaced the brush 104 along the longitudinal direction 210.

FIG. 4A and FIG. 4B illustrate an actuator that comprises a magnetic knob 402 disposed on the exterior surface 204 of the shell 112, which is configured to magnetically couple to a magnet 404 fixed to a slide-mechanism 406 slideably housed in the shell 112 through the exterior surface 204 of the shell 112. FIG. 4B illustrates the magnetic knob 402 having a magnet 408 disposed on a bottom surface 410 of the magnetic knob 402. Further, FIGS. 4A and 4B illustrate a track 412 configured to linearly guide the magnetic knob 402 on the exterior surface 204 of the shell 112. With the magnetic knob 402 magnetically coupled to the slide-mechanism 406 slideably housed in the shell 112, and the magnetic knob 402 slideably disposed on the exterior surface 204 of the shell 112 via the track 412, the compact 110 is configured to slide a magnetic brush (e.g., magnetic brush 104) into and out of the shell 112.

FIGS. 4C and 4D illustrate an embodiment of an actuator that comprises a dial 414 disposed on the exterior surface 204 of the shell 112 and is configured to rotate in a clockwise and/or counter-clockwise direction. Further, FIG. 4C and FIG. 4D illustrate a magnet 416 housed in the shell 112 configured to rotate in the clockwise and/or counter-clockwise direction of the dial 414 for magnetically coupling or repelling a slide-mechanism 418. While, FIG. 4C and FIG. 4D illustrate magnet 416 for magnetically coupling or decoupling to the slide-mechanism 418, magnet 416 may alternatively magnetically couple to a magnetic brush, instead of magnetically coupling with the slide-mechanism 418. FIG. 4D illustrates an axle 420 configured to be received by an opening 422 disposed in the exterior surface 204 of the shell 112. The axle 420 is illustrated as coupling the dial 414 disposed on the exterior surface 204 of the shell 112 and the magnet 416 housed in the shell 112. With the dial 414 coupled to the magnet 416 via the axle 420, and with the magnet 416 is configured to rotate in the clockwise and/or counter-clockwise direction of the dial, the compact is configured to slide a magnetic brush (e.g., magnetic brush 104) into and out of the shell 112. For example, when an opposite pole of magnet 416 is selectively rotated into a position facing an opposite pole of a magnet 424 fixed in the slide-mechanism 418 having a magnetic brush attached thereto, the magnet 416 attracts and magnetically couples to magnet 424. The magnetic attraction between magnet 416 and magnet 424 slides the magnetic brush into the shell 112 and into the stored position (e.g., as illustrated in FIG. 2C). However, when a like pole of magnet 416 is selectively rotated into a position facing a like pole of magnet 424 fixed in the slide-mechanism 418, the magnet 416 repels and slideably displaces magnet 424. The magnetic repulsion between magnet 416 and magnet 424 slides the magnetic brush into an accessible position (e.g., as illustrated in FIG. 2B).

FIGS. 4E and 4F illustrate an embodiment of an actuator that comprises a dial 426 disposed on another exterior surface 428 of the shell 112 and is configured to rotate in a clockwise and/or counter-clockwise direction. Further, FIG. 4E and FIG. 4F illustrate a gear-mechanism 430 housed in the shell 112, which is configured to slide a magnetic brush (e.g., magnetic brush 104) into and out of the shell 112, when the dial 426 is rotated in the clockwise and/or counter-clockwise direction. FIG. 4E and FIG. 4F illustrate an axle 432 configured to be received by an opening 434 disposed in the other exterior surface 428 of the shell 112. The axle 432 is illustrated as coupling the dial 426 disposed on the other exterior surface 428 of the shell 112 and the gear-mechanism 430 housed in the shell 112. Further, FIG. 4E and FIG. 4F illustrate the gear-mechanism 430 coupled to a slide-mechanism 436. With the axle 432 coupling the dial 426 to the gear-mechanism 430 and the gear-mechanism 430 coupled to the slide-mechanism 436, the compact 110 is configured to slide a magnetic brush (e.g., magnetic brush 104) into and out of the shell 112.

While FIG. 4A and FIG. 4B, FIGS. 4C and 4D, and FIG. 4E and FIG. 4F illustrate back views and top views of other actuators, respectively, that may be used to linearly displaced a magnetic brush within the shell 112 of the compact 110, other actuators are contemplated. For example, an embodiment of an actuator that comprises a push-button disposed on an exterior surface of the shell configured to activate a spring-mechanism housed in the shell. In this embodiment, the push-button and the spring-mechanism are coupled via a linkage, where the linkage is fixed to a bottom of the push-button and to a top of the spring-mechanism. Again, as discussed above, the linkage is configured to be received by an opening disposed in the exterior surface of the shell comprising the push-button. Here, in this embodiment, the spring-mechanism may be coupled to a slide-mechanism for sliding a magnetic brush into and out of a shell of a compact.

Further, it also is contemplated that a locking mechanism may also be included with the embodiments as discussed above. The locking mechanism being configured to temporarily lock a slide-mechanism and likewise a magnetic brush magnetically coupled to the slide-mechanism in a stored position, keeping the magnetic brush from inadvertently sliding out of the compact. In addition to the locking mechanism, a complementary un-locking mechanism is also conceptualized. The un-locking mechanism may un-lock the locking mechanism by way of selectively activating an actuator (e.g., actuator 202) for an additional time (e.g., much like the locking and un-locking of a retractable ball-point pen). Alternatively, the locking mechanism and un-locking mechanism may be by way of a snap fit, press fit, or the like, of the linkage 216 to the exterior surface 204 of the shell 112.

Exemplary Method of Using Compact System

Figure 5:
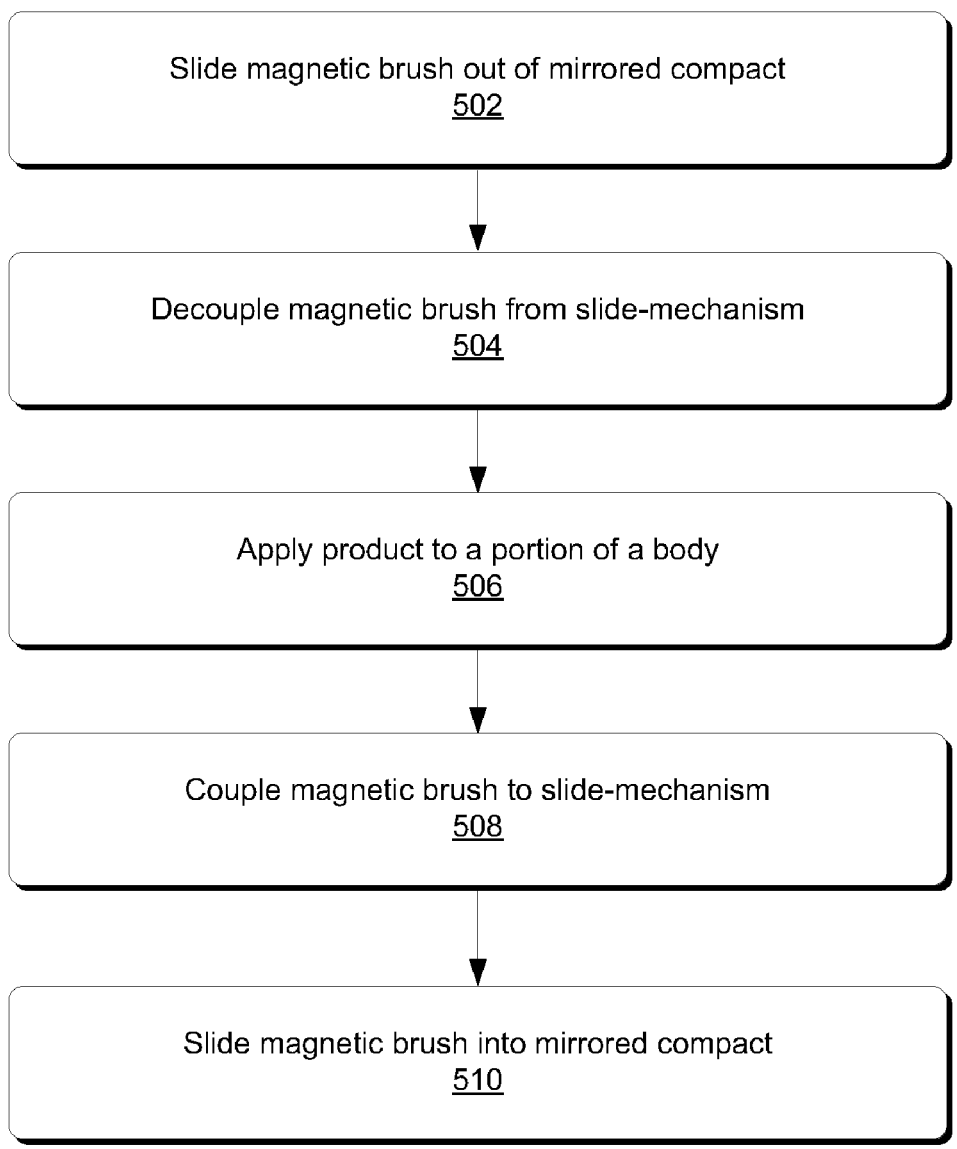
FIG. 5 is a flow diagram of an illustrative process for using the compact system of FIG. 1.

FIG. 5 is a flow diagram of an example process 500 which may, but need not necessarily be performed using the compact system 102 of FIG. 1. For convenience, the process 500 will be described with reference to the compact 110 and magnetic brush 104 as illustrated in FIG. 1, but the process 500 is not limited to use with these implements. For instance, a user may perform this process 500 to apply a blush to a chin, or a user may perform this process to remove a substance from a body. In some instances, the user may perform this process in a manufacturing environment, in a commercial environment (e.g., beauty salon), or in a place of residence. While FIG. 5 illustrates a process 500 for applying product to a portion of a face, it is to be appreciated that this process may apply to applying any type substances to any type of body (e.g., applying finger print dust at a crime scene).

Process 500 includes an operation 502, which represents sliding a magnetic brush (e.g., magnetic brush 104) via an actuator (i.e., any of actuators 202, 414, 428, or the like) from a stored position (e.g., as illustrated in FIG. 2C) within a compact (e.g., compact 110), such that, a portion (e.g., portion 230) of the brush is exposed (e.g., as shown in FIG. 2B). Next, operation 504 represents decoupling the magnetic brush from a slide-mechanism (e.g., as illustrated in FIG. 2A). Operation 504 is followed by operation 506, which represents applying a product (e.g., a powder, a cream, or a liquid) to a portion of the body. Next, process 500 proceeds to operation 508, which represents coupling the decoupled magnetic brush to the slide-mechanism. Process 500 is complete when, at operation 510, a user selectively displaces the magnetic brush, again via the actuator, back into the stored position.

CONCLUSION

Although embodiments have been described in language specific to structural features and/or methodological acts, it is to be understood that the disclosure is not necessarily limited to the specific features or acts described. Rather, the specific features and acts are disclosed as illustrative forms of implementing the embodiments. For example, in various embodiments, any of the structural features and/or methodological acts described herein may be rearranged, modified, or omitted entirely. For example, the shape, size, and configuration of the magnetic brush, compact, and actuator may be varied.

What is claimed is:

1. An applicator system for applying a product to a body comprising:
   a brush for applying the product to the body comprising:
   a base having a top and bottom;
   a group of bristles fixed in a pocket in the top of the base; and
   a magnet fixed to a gripping portion of the bottom of the base opposite the group of bristles; and
   a compact having a top and a bottom and housing the brush, the compact comprising:
   a shell defining a cavity for receiving the brush;
   a slide-mechanism housed in the shell for sliding the brush into and out of the shell;
   an actuator disposed on an exterior surface of a wall of the shell for selectively sliding the slide-mechanism housed in the shell; and
   another magnet fixed to a portion of the slide-mechanism housed in the shell for magnetically coupling with the magnet fixed to the rear portion of the brush to releasably couple the brush to the compact.

2. The applicator system according to claim 1, wherein the compact further comprises a mirror disposed on an exterior surface of another wall of the shell opposite to the actuator.

3. The applicator system according to claim 2, wherein the compact further comprises a compartment arranged between the mirror and the another wall of the shell opposite the actuator.

4. The applicator system according to claim 1, wherein the compact further comprises a linkage configured to be received by a slot disposed in the exterior surface of the shell, wherein the linkage couples the actuator and the slide-mechanism.

5. The applicator system according to claim 1, further comprising a locking mechanism to hold the brush in place and to keep the slide-mechanism from inadvertently sliding the brush into or out of the compact.

6. The applicator system according to claim 1, wherein the base of the brush comprises a flat body having a rectangular cross-section as viewed from the bottom.

7. The applicator system according to claim 6, wherein the rectangular cross-section of the base as viewed from the bottom comprises a width approximately ten times greater than a height.

8. The applicator system according to claim 6, wherein the rectangular cross-section of the base as viewed from the bottom comprises a width of approximately 52 millimeters and a height of approximately 5 millimeters.

9. The applicator system according to claim 1, wherein the shell of the compact comprises a flat body having a rectangular cross-section as viewed from the top.

10. The applicator system according to claim 9, wherein the rectangular cross-section of the shell as viewed from the top comprises a width approximately seven times greater than a height.

11. The applicator system according to claim 9, wherein the rectangular cross-section of the shell as viewed from the top comprises a width of approximately 55 millimeters and a height of approximately 8 millimeters.

12. The applicator system according to claim 1, wherein the product comprises a powder, a cream, or a liquid.

13. A compact comprising:
    an applicator comprising a magnet fixed to a bottom of a base and an application surface fixed to a top of the base, the applicator for applying product to a body;
    a shell defining a cavity for removably housing the applicator;
    a slide-mechanism housed in the shell comprising another magnet fixed to a portion of the slide-mechanism for magnetically coupling with the magnet fixed to the bottom of the base of the applicator to releasably couple the applicator to the slide-mechanism; and an actuator slideably disposed on an exterior surface of a wall of the shell for selectively sliding the applicator into and out of the shell.

14. The compact according to claim 13, wherein the compact further comprises a mirror disposed on an exterior surface of another wall of the shell opposite to the actuator.

15. The compact according to claim 13, wherein the compact further comprises a linkage configured to be received by a slot disposed in the exterior surface of the shell comprising the actuator, wherein the linkage couples the actuator and the slide-mechanism.

16. The compact according to claim 13, wherein the application surface fixed to the top of the base comprises a flat fan-shaped group of bristles.

17. The compact according to claim 13, wherein the application surface fixed to the top of the base comprises a brush, a sponge, a flocking, or a combination thereof.

18. A compact comprising:
   a shell defining a substantially rectangular receptacle;
   a slide-mechanism slideably housed in the shell, wherein the slide-mechanism comprises a magnet;
   an applicator removably attached to the slide-mechanism and housed in the substantially rectangular receptacle of the shell; and
   an actuator disposed on an exterior surface of the shell for selectively sliding the slide-mechanism slideably housed in the shell to move the applicator in and out of the shell.

19. The compact according to claim 18, further comprising a mirror disposed on an exterior surface of the shell opposite to the exterior surface of the shell comprising the actuator.

20. The compact according to claim 18, further comprising a linkage configured to be received by a slot disposed in the exterior surface of the shell, the linkage being fixed to a bottom of the actuator and to a top of the slide-mechanism.

21. The compact according to claim 18, wherein the actuator comprises a magnetic knob slideably disposed on the exterior surface of the shell and configured to magnetically couple to the slide-mechanism slideably housed in the shell through the exterior surface of the shell.

22. The compact according to claim 18, wherein the actuator comprises a dial disposed on the exterior surface of the shell configured to extend and/or retract the applicator.

23. The compact according to claim 18, wherein the actuator comprises:
   a push-button disposed on the exterior surface of the shell; and
   a spring-mechanism housed in the shell configured to slide the brush out of the shell when the push-button is actuated.

24. The compact according to claim 18, wherein the applicator comprises a brush, a sponge, a flocking, or a combination thereof.

25. The compact according to claim 18, wherein the applicator is removably attached to the slide-mechanism by a magnet, a snap fit, or a clip.

* * * * *